United States Patent [19]

Vincent

[11] Patent Number: 6,149,948

[45] Date of Patent: Nov. 21, 2000

[54] METHOD OF DECREASING PLASMA CHOLESTEROL AND TRIGLYCERIDES WITH A CHROMIUM-CONTAINING COMPLEX

[75] Inventor: John B. Vincent, Tuscaloosa, Ala.

[73] Assignee: University of Alabama, Tuscaloosa, Ala.

[21] Appl. No.: 09/406,775

[22] Filed: Sep. 28, 1999

Related U.S. Application Data

[60] Provisional application No. 60/142,065, Jul. 2, 1999.

[51] Int. Cl.$^7$ ..................................................... A61K 33/24
[52] U.S. Cl. ......................... 424/655; 424/617; 514/492; 514/505
[58] Field of Search ................................... 514/492, 505; 424/617, 655

[56] References Cited

U.S. PATENT DOCUMENTS 5,872,102   2/1999   Vincent et al. ............................ 514/21

FOREIGN PATENT DOCUMENTS 0 037 144 A2   7/1981   WIPO .

OTHER PUBLICATIONS

T. Yosida et al., "High Magnetic Field Study of Chromium Trimer Complexes Below 1 K", *Journal of the Physical Society of Japan*, Apr. 1988, vol. 57, No. 4, pp. 1428–1434.

N. Mirsky et al., "Chromium in Biological Systems, I. Some Observations on Glucose Tolerance Factor in Yeast", *Journal of Inorganic Biochemistry*, 1980, vol. 13, pp. 11–21.

H. Nishimura et al., "Anomalous G–Value of a Cr–Trimer Complex, Cr–Propionate $\{Cr_3O(C_2H_5COO)_6(H_2O)_3\}NO_3 2H_2O$", *Journal of the Physical Society of Japan*, Jan. 1985, vol. 54, No. 1, pp. 395–399.

A. v.d. Bergen et al., "Electrospray Mass Spectrometric Study of $[M_3O(RCOO)_6L_3]^+$ Cations (M=Cr, Fe; L=$H_2O$, MeOH, py)", *American Chemical Society*, 1993, vol. 32, pp. 3408–3411.

M. Honda et al., "Electron Spin Resonance in Cr–Trimer Complexes", *Journal of the Physical Society of Japan*, Oct. 1992, vol. 61, No. 10, pp. 3773–3785.

A. Earnshaw et al., "Chemistry of Polymer Nuclear Compounds. Part VI* Magnetic Properties of Trimeric Chromium and Iron Carboxylates", *J. Chem. Soc (A)*, 1966, pp. 1656–1663.

M. Glass et al., "Nuclear Magnetic Resonance Studies of Multinuclear Chromium Assemblies", *Polyhedron*, 1993, vol. 12, No. 2, pp. 133–140.

Yu, "Study on the Dual MU . . . ", *Hua Hsueh Hsueh Pao. Acta Chimica Sinica*, 1993, vol. 51, No. 6, pp. 579–585.

J. Vincent, "Heterotrinuclear Carboxylates of Chromium(III) and Iron(III): Mixtures or Pure Compounds?", *Inorg. Chem.*, 1994, vol. 33, pp. 5604–5606.

J. K. Speetjens et al., "The Nutritional Supplement Chromium(III) Tris(Picolinate) Cleaves DNA", *Chemical Research in Toxicology*, Jan. 28, 1999, vol. 12, No. 6, pp. 483–487.

J. Vincent, "Mechanisms of Chromium Action: Low–Molecular–Weight Chromium–Binding Substance", *Journal of the American College of Nutrition*, 1999, vol. 18, No. 1, pp. 6–12.

C. Davis et al., "Synthetic Multinuclear Chromium Assembly Activates Insulin Receptor Kinase Activity: Functional Model for Low–Molecular–Weight Chromium–Binding Substance", *Inorganic Chemistry*, May 14, 1997, vol. 36, No. 23, pp. 5316–5320.

R. Anderson et al., "Dietary Chromium Effects on Tissue Chromium Concentrations and Chromium Absorption in Rats", *The Journal of Trace Elements in Experimental Medicine*, 1996, vol. 9, pp. 11–25.

M. Morita et al., "$N_2$ Laser–Excited Luminescence of Antiferromagnetically Coupled Trinuclear Chromium(III) Complexes", *International Journal of Quantum Chemistry*, 1980, vol. XVIII, pp. 625–631.

G. Fu et al., "Fast Atom Bombardment Mass Spectra of Trinuclear .MU .3–OXO–Carboxylato Complexes of Chromium", *Jiegou Huaxue (J. Struct. Chem.)*, 1990, vol. 9 No. 4.

M. K. Johnson et al., "Vibrational Spectra of Carboxylato Complexes–III. Trinuclear 'Basic' Acetates and Formates of Chromium(III), Iron(III) and Other Transition Metals", *Spectrochimica Acta.*, 1981, vol. 37A, No. 11, pp. 995–1006.

*Primary Examiner*—Marianne M. Cintins
*Assistant Examiner*—C. Delacroix-Muirheid
*Attorney, Agent, or Firm*—Oblon, Spivak, McClelland, Maier & Neustadt, P.C.

[57] ABSTRACT

A method of decreasing plasma cholesterol and/or triglycerides, comprising administering an effective amount of $[Cr_3O(O_2CCH_2CH_3)_6(H_2O)_3]^+$ to a patient in need thereof.

17 Claims, 10 Drawing Sheets

METHOD OF DECREASING PLASMA CHOLESTEROL AND TRIGLYCERIDES WITH A CHROMIUM-CONTAINING COMPLEX

This Application claims benefit of priority to U.S. Provisional Application Serial No. 60/142,065, filed on Jul. 2, 1999. The contents of the Provisional Application are incorporated herein by reference.

BACKGROUND OF THE INVENTION

1. Field of the Invention

The present invention relates to methods of using the chromium(III) complex represented by the formula $[Cr_3O(O_2CCH_2CH_3)_6(H_2O)_3]^+$ to reduce plasma levels of cholesterol and triglycerides. The invention also includes compositions which contain this chromium(III) complex.

2. Background of the Invention

In the late 1950s and 1960s, rats fed a chromium-deficient diet were found to possess a decreased ability to repress blood glucose concentrations, while chromic ions were shown to increase the efficiency of insulin action in rat epididymal tissue [1–5]. Since these observations, a search has been underway to identify the biologically active form of chromium, that is, the biomolecule which naturally binds chromium (III) and possesses an intrinsic function associated with insulin action in mammals [6–8]. Subsequent demonstration that the populations of developed nations intake on average less than the recommended safe and adequate amount of chromium in their daily diet [9, 10] has resulted in the development of chromium-containing dietary supplements. Such materials also have potential as insulin-potentiating therapeutics which could possibly see use in the treatment of diabetes [11]. Determining the structure, function, and mode of action of the biologically active form of chromium could greatly aid in the rational design of such potential therapeutics.

The first chromium-containing species proposed to be biologically active was glucose tolerance factor(GTF)[1,12]. GTF was first isolated from acid-hydrolyzed porcine kidney powder, although a similar, if not identical, material was subsequently isolated from yeast[1,13]. Currently the term GTF is usually understood to refer to only the material isolated from yeast. GTF is absorbed better than simple chromic salts and potentiates insulin action in rat epididymal tissue or isolated rat adipocytes [14]. However, kinetics studies indicate that GTF does not intrinsically possess biological activity [15]; additionally, the material is apparently a byproduct of the acid hydrolysis step used in its purification [16].

GTF was proposed to be composed of chromic ion, nicotinic acid, and the amino acids glycine, glutamic acid and cysteine [13]. While these results have not been reproducible in some laboratories [17–21], this report stimulated an intense interest in the synthesis of chromic-nicotinate complexes [22–25], some of which have been patented as nutritional supplements. The proposed identification of nicotinic acid (2-carboxypyridine) also stimulated investigations of complexes of chromium(III) with the related pyridine carboxylic acids picolinic acid (2-carboxypyridine) and isonicotinic acid (4-carboxypyridine) [26–28]. As a result chromium(III) tris(picolinate), $Cr(pic)_3$, has become a very popular nutritional supplement and is being tested as a therapeutic for the treatment of symptoms of adult-onset diabetes. It is available over-the-counter in the form of pills, chewing gums, sport drinks, and nutrition bars. $Cr(pic)_3$ is also a well absorbed form of chromium and has been proposed to be the biologically active form of chromium [29]. This is, however, extremely doubtful given the chemistry required to synthesize this material.

In the last decade, a number of investigators have examined the effects of administering $Cr(pic)_3$ (and in some cases other forms of chromium(III)) to rats on regular diets [30–33]. After an initial preliminary report which suggested beneficial effects on blood variables [30], detailed examinations of the effect of $Cr(pic)_3$ administration in amounts up to 1500 $\mu$g/kg diet for up to 24 weeks have found no acute toxic effects [31–33]. However, the compound and other chromium sources examined (most notably "Cr nicotinate" and chromium chloride) also had no effect on body mass, percentage lean or fat content, tissue size (heart, testes, liver, kidney, muscle, epididymal fat, spleen, and kidney), or blood variables (fasting glucose, insulin, cholesterol, etc.). No differences in the gross histology of the liver or kidney (organs where chromium(III) preferentially accumulated) were found, although chromium did accumulate in these organs [33]. Another study compared the effects of a Cr-deficient diet with diets supplemented with ten different sources of chromium, including allowing rats to live in stainless steel cages. The Cr sources had no effect on body mass; all but one source decreased epididymal fat. Testes and liver masses tended to be lowered, whereas kidney, heart, and spleen masses were not significantly altered. Supplemental Cr had no effect on serum triglycerides or cholesterol, and only one source resulted in lower serum glucose [34]. While these studies did not manifest any acute toxicity, the lack of beneficial effects of $Cr(pic)_3$ supplementation on growth, fat content or glucose, insulin, or cholesterol concentrations raises questions about its therapeutic potential. Recently the safety of intaking $Cr(pic)_3$ has been questioned, especially in regards to its potential to cause clastogenic damage [35,36]. At physiologically-relevant concentrations of chromium (120 nM) and biological reductants such as ascorbic acid and thiols (5 mM), $Cr(pic)_3$ has been shown to catalytically produce hydroxyl radicals which cleave DNA[35]. This ability stems from the combination of chromium and picolinate; the picolinate ligands prime the redox potential of the chromic center such that it is susceptible to reduction. The reduced chromium species interacts with dioxygen to produce reduced oxygen species including hydroxyl radical. These studies are in agreement with earlier studies which showed that mutagenic forms of chromium(III) required chelating ligands containing pyridine-type nitrogens coordinated to the metal [37].

Recently the naturally-occurring oligopeptide low-molecular-weight chromium-binding substance, LMWCr, has been proposed as a candidate for the biologically active form of chromium [6,7,38,39]. Kinetics studies of insulin action on rat adipocytes suggest that LMWCr has an intrinsic function in insulin-sensitive cells [15,40]. The oligopeptide appears to be part of an insulin signal amplification mechanism [6,7]. The oligopeptide containing four chromic ions binds to insulin-activated insulin receptor, stimulating its tyrosine kinase activity up to eight-fold with a dissociation constant of approximately 100 pM [38]. Spectroscopic studies have shown that LMWCr possesses a multinuclear chromic assembly where the chromic centers are bridged by anionic ligands (presumably oxide and/or hydroxide). The assembly is supported by carboxylate groups from aspartate and glutamate residues from the oligopeptide [41]. This discovery has spurred an interest in the synthesis and characterization of multinuclear oxo(hydroxo)-bridged chromium(III) carboxylate assembles [42–45]. In 1997, such an assembly, $[[Cr_3O(O_2CCH_2CH_3)_6(H_2O)_3]^+$, 1, was found to mimic the ability of LMWCr to stimulate insulin receptor kinase activity [39]. Both LMWCr and the biomimetic 1 have been proposed as potential nutritional supplements and therapeutics. Both LMWCr and 1 have been shown not to lead to DNA cleavage [46]. The synthetic complex has several potential benefits over the natural material: it is inexpensive to synthesize and can be readily prepared in bulk. LMWCr is susceptible to hydrolysis, especially in the presence of acid, whereas the synthetic material can be recrystallized from dilute mineral acid [47] and could potentially survive oral ingestion. After the insulin signaling event, LMWCr may be excreted in the urine [48,49], and it is possible the body might target the material for excretion rather than absorption.

SUMMARY OF THE INVENTION

The present invention is based on the discovery that the chromium(III) complex having the formula $[Cr_3O(O_2CCH_2CH_3)_6(H_2O)_3]^+$, hereafter referred to as complex or compound 1, effectively lowers triglyceride and/or cholesterol levels. Complex 1 is particularly useful since, in addition to having the ability to lower triglyceride and/or cholesterol levels, the complex is stable under acidic conditions, is readily and inexpensively synthesized, and does not have toxic side effects, such as causing DNA cleavage.

Accordingly, based on the above-described discovery, the present invention provides a method of decreasing plasma cholesterol and/or triglycerides, comprising administering an effective amount of $[Cr_3O(O_2CCH_2CH_3)_6(H_2O)_3]^+$ to a patient in need thereof.

The present invention also provides a composition, comprising:

$[Cr_3O(O_2CCH_2CH_3)_6(H_2O)_3]^+$, and at least one additional agent which is capable of reducing levels of plasma cholesterol and/or triglycerides.

BRIEF DESCRIPTION OF THE FIGURES

A more complete appreciation of the invention and many of the attendant advantages thereof will be readily obtained as the same becomes better understood by reference to the following detailed description when considered in connection with the accompanying figures, wherein.

Reactions were allowed to proceed 180 minutes before quenching by addition of loading buffer.

Figure 5:
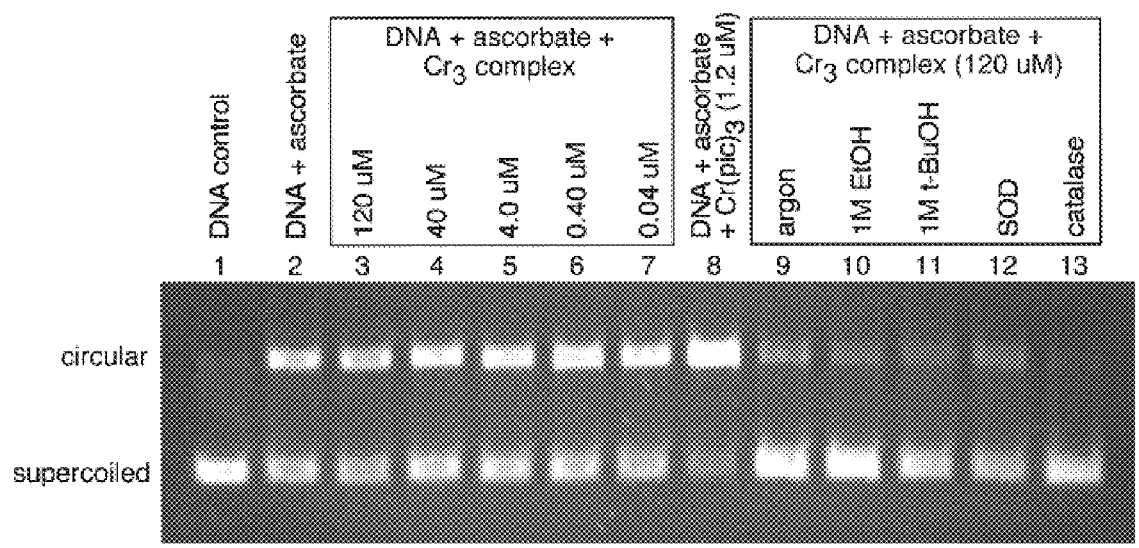

FIG. 5: Cleavage of pUC19 by LMWCr. The reactions contain pUC19 (39 $\mu$M in base pairs) and 50 mM phosphate buffer, pH 7.0 and: Lane 2, 5 mM ascorbate; Lane 3, 90 $\mu$M LMWCr and 5 mM ascorbate; Lane 4, 30 $\mu$M LMWCr and 5 mM ascorbate; Lane 5, 3.0 $\mu$M LMWCr and 5 mM ascorbate; Lane 6, 0.30 $\mu$M LMWCr and 5 mM ascorbate; Lane 7, 0.030 $\mu$M LMWCr and 5 mM ascorbate; Lane 8, 5 mM ascorbate and 1.2 $\mu$M Cr(pic)$_3$; Lane 9, 90 $\mu$M LMWCr and 5 mM ascorbate under argon; Lane 10, 90 $\mu$M LMWCr, 5 mM ascorbate, and 11 M EtOH; Lane 11, 90 $\mu$M LMWCr, 5 mM ascorbate, and 1 M t-BuOH; Lane 12, 90 $\mu$M LMWCr, 5 mM ascorbate, and 100 $\mu$g/mL SOD; Lane 13, 90 $\mu$M LMWCr, 5 mM ascorbate, and 100 $\mu$g/mL catalase. Reactions were allowed to proceed 60 minutes before quenching by addition of loading buffer.

Figure 6:
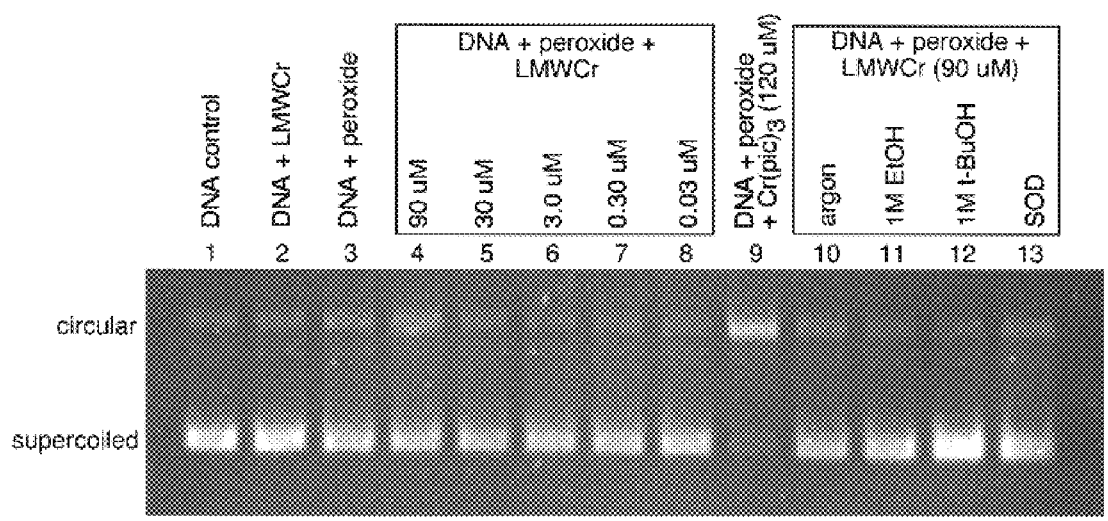

FIG. 6: Cleavage of pUC19 by LMWCr. The reactions contain pUC19 (39 $\mu$M in base pairs) and 50 mM phosphate buffer, pH 7.0 and: Lane 2, 90 $\mu$M LMWCr; Lane 3, 215 $\mu$M H$_2$O$_2$; Lane 4, 90 $\mu$M LMWCr and 215 $\mu$M H$_2$O$_2$; Lane 5, 30 $\mu$M LMWCr and 215 $\mu$M H$_2$O$_2$; Lane 6, 3.0 $\mu$M LMWCr and 215 $\mu$M H$_2$O$_2$; Lane 7, 0.30 $\mu$M LMWCr and 215 $\mu$M H$_2$O$_2$; Lane 8, 0.03 $\mu$M LMWCr and 215 $\mu$M H$_2$O$_2$; Lane 9, 120 $\mu$M Cr(Pic)$_3$ and 215 $\mu$M H$_2$O$_2$; Lane 10, 90 $\mu$M LMWCr and 215 $\mu$M H$_2$O$_2$ under argon; Lane 11, 90 $\mu$M LMWCr, 215 $\mu$M H$_2$O$_2$, and 1 M EtOH; Lane 12, 90 $\mu$M LMWCr, 215 $\mu$M H$_2$O$_2$, and 1 M t-BuOH; Lane 13, 90 $\mu$M LMWCr, 215 $\mu$M H$_2$O$_2$, and 100 $\mu$g/mL SOD.

Reactions were allowed to proceed 180 minutes before quenching by addition of loading buffer.

Figure 7A:
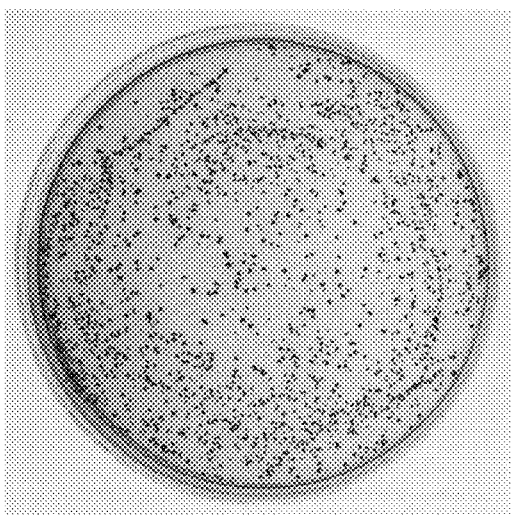
Figure 7B:
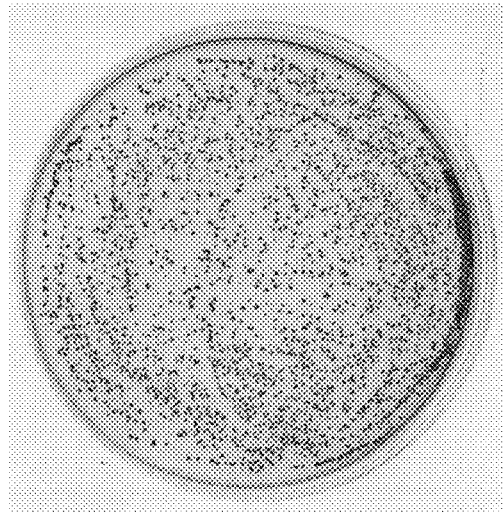

FIGS. 7(A and B): LB-ANM plates of DH5$\alpha$ E. coli colonies transformed with (A) complex 1-nicked pUC19 and (B) supercoiled pUC19. The plates were supplemented with 30 $\mu$g $\mu$L$^{-1}$ of X-gal and 100 $\mu$M IPTG in order to better visualize the colonies.

Figure 8:
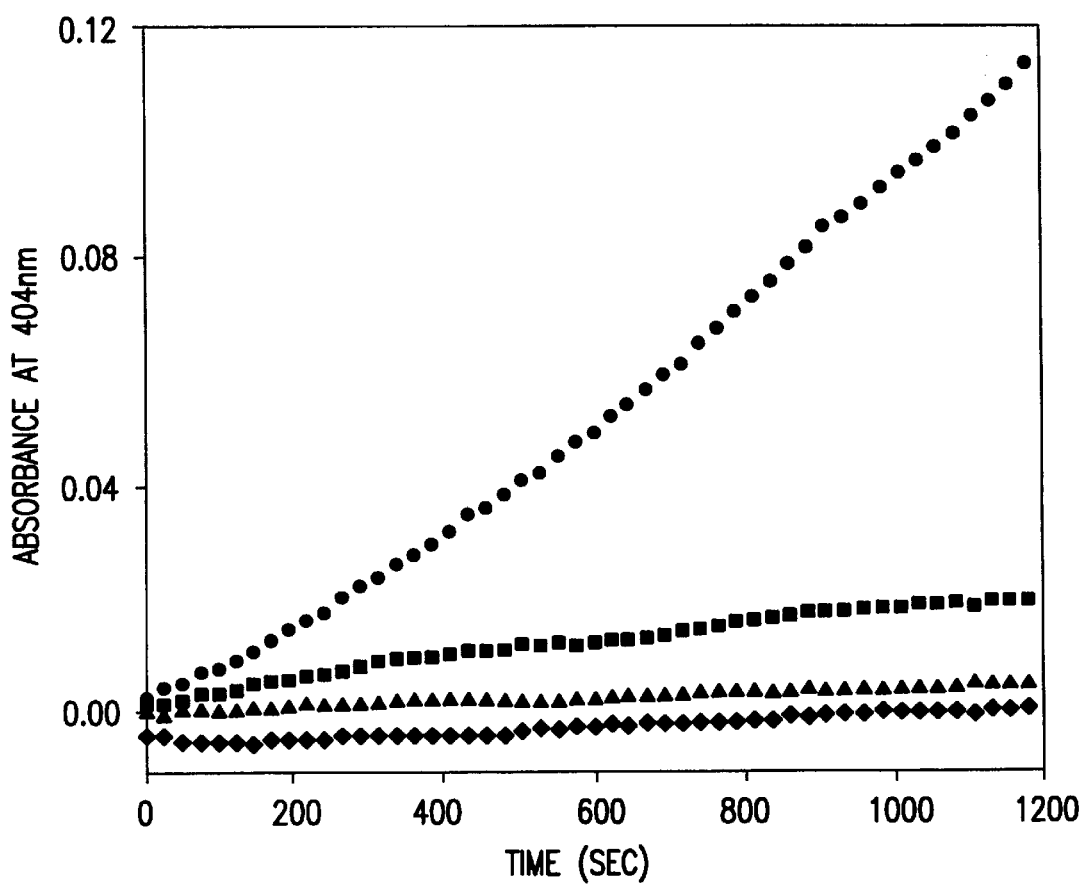

FIG. 8: Hydrolysis of bis-p-nitrophenyl phosphate catalyzed by complex 1. Reactions were conducted in 0.010 M Tris, pH 8.0 at 25° C. The reaction (♦) contained 2.5 mM bis-p-nitrophenyl phosphate and buffer; reaction (▲) contained 2.5 MM bis-p-nitrophenyl phosphate, buffer, and 900 $\mu$M H$_2$O$_2$; reaction (■) contained 2.5 mM bis-p-nitrophenyl phosphate, 1.5 mM complex, and buffer; and reaction (●) contained 2.5 MM bis-p-nitrophenyl phosphate, 1.5 mM complex, 900 $\mu$M H$_2$O$_2$, and buffer.

DETAILED DESCRIPTION OF THE INVENTION

Complex 1 is administered to a subject, e.g., a patient, in order to reduce the level of plasma cholesterol or triglycerides, or both. Administering complex 1 may result in decreased plasma cholesterol levels or decreased plasma triglycerides levels. Administering the complex may also result in decreased plasma cholesterol levels and plasma triglycerides levels. Complex 1 may be administered to reduce the level of total cholesterol, including LDL cholesterol and HDL cholesterol.

Suitable patients include those diagnosed with elevated levels of plasma cholesterol or triglycerides, or both. The patient may be a mammal. In one embodiment, the patient is a human being. In another embodiment, the patient is an animal, such as a dog, cat, cow, horse, chicken, turkey, sheep or a goat.

The dose of complex 1 administered to the patient, may vary widely. For example, complex 1 may be administered at a dose of 1 to 1500 µg/kg body mass per dose. Other suitable dosages include 10 to 1000 µg/kg body mass, 10 to 500 µg/kg body mass and 10 to 250 µg/kg body mass. Typically, the complex will be administered on a daily basis for a time sufficient to decrease the levels of plasma cholesterol and/or triglycerides to desired levels. Plasma cholesterol and/or triglycerides levels may be monitored using any of the well-established techniques available for this purpose.

Chromium complex 1 may administered in the form of a food product, i.e., a composition containing the complex and at least one food. The complex may be administered to the patient by injection, I.V. or oral administration as, for example, an aqueous solution or suspension. These solutions and suspensions may contain all of the customary additives well known to those of skill in the art, e.g., buffering agents, salts (e.g., NaCl), sugars (e.g., glucose and lactose), etc. Alternatively, the complex can be formulated into a solid dosage form, such as a tablet, pill, capsule or caplet, suitable for oral ingestion. The daily dosage of complex 1 may vary over a wide range, such as 5 to 600 micrograms of Cr per day, including all specific values and subranges therebetween.

Complex 1 may also be used as a component of an animal nutrient composition suitable for human and/or animal consumption. Such a composition contains chromium complex 1 and at least one pharmacologically acceptable excipient. Suitable excipients are well-known and include diluents, disintrgrators, binders and lubricants (glidants). Specific examples include, for example, celluloses, gelatins, starches, polysorbate 80, oils (e.g., peanut oil, fish liver oil). Preferably, the nutritive composition is made to U.S. Pharmacopiea quality, purity and potency standards. The nutrient composition is preferably in the form of a solid. For a description of solid compositions, see Pharmaceuticals, Kirk-Othmer Encyclopedia of Chemical Technology, Fourth Edition, Volume 18, pp. 480–510, incorporated herein by reference.

The nutritive composition may also contain at least one additional animal nutrient. As used herein the term "animal nutrient" refers to compounds and substances which are recognized to maintain and regulate bodily functions. Specific examples of additional animal nutrients include vitamins (e.g., vitamin A, beta carotene, vitamin $B_1$, vitamin $B_2$, vitamin $B_6$, vitamin $B_{12}$, vitamin C, vitamin D, vitamin E, vitamin K), minerals (e.g., calcium, iron, copper, selenium, zinc, magnesium), enzyme cofactors, iodine, phosphorous, folate, biotin, and niacin.

Complex 1 may also be used as a component of a composition which also contains at least one additional agent which is capable of reducing levels of plasma cholesterol and/or triglycerides. This additional agent may be a compound which suppresses cholesterol biosynthesis. Compounds which suppresses cholesterol biosynthesis include inhibitors of β-hydroxy-β-methyl gluterate-coenzyme A (HMG-CoA) reductase, acyl CoA-acyl transferase (ACAT). Specific example of such compounds include mevinolin and probucol. Kirk-Othmer Encyclopedia of Chemical Technology, Fourth Edition, Volume 5, pp. 207–300, incorporated herein by reference.

This composition may be suitable for pharmaceutical use, and composition may also contain any of the well-recognized excipients discussed above. The pharmaceutical composition is preferably in a solid dosage form as discussed above. Such agents are described in Kirk-Othmer Encyclopedia of Chemical Technology, Fourth Edition, Volume 18, pp. 480–553, incorporated herein by reference.

Since complex 1 is a cation, the complex will, of course, be in the form of a salt with an anion. The anion should be non-toxic when used in the methods according to the present invention, i.e., the anion is pharmacologically acceptable. The anion is preferably the salt of a pharmacologically acceptable inorganic or organic acid. Specific examples of suitable anions include nitrate, sulfate, chloride, bromide, iodide, and phosphate.

The plasma level of cholesterol and/or triglycerides in the patient may be reduced by at least 10% by administering the complex 1, relative to the levels prior to beginning administration of the complex. Preferably, the levels are reduced at least 20%, more preferably at least 40%, and, most preferably more than 40%, relative to the levels prior to beginning administration of the complex. The percentage reduction may be 50%, 60% 70% or higher.

EXAMPLES

Having generally described this invention, a further understanding can be obtained by reference to certain specific examples which are provided herein for purposes of illustration only and are not intended to be limiting unless otherwise specified.

Example 1

In Vivo Studies With Complex 1
LMWCr and $[Cr_3O(O_2CCH_2CH_3)_6(H_2O)_3]^+$

LMWCr was obtained as previously described [41]. Oligopeptide concentration was determined by the fluorescamine procedure of Undenfriend and coworkers using glycine as standard [50] or by measuring chromium content by the diphenylcarbazide method [51] using the method of standard addition to minimize any matrix effects and assuming a chromium to oligopeptide ratio of 4 to 1. Compound 1 was prepared as described in the literature [52]. For all experiments solutions of LMWCr or 1 were prepared by dilutions of more concentrated stock solutions. All operations were performed with doubly deionized water unless otherwise noted.

Animals

Four week old male Sprague Dawley rats were allowed to fed ad libitum on a commercial rat food and tap water. Rats were raised in standard plastic and stainless steel cages on a 12 hour light-dark cycle. Solid food intake and body mass were monitored daily. Twenty four rats were divided randomly into three groups of eight. The first group was injected daily in the tail vein with 200 µL of an aqueous solution containing LMWCr to give a total amount of chromium equivalent to 20 µg per kilogram body weight; the second group received 200 pL of an aqueous solution of compound 1 to give a total amount of chromium equivalent to 20 µg per kg body mass. The last group was injected with 200 µL of doubly deionized water daily and served as the control. After 12 weeks, the animals were sacrificed by carbon dioxide asphyxiation. Liver, kidney, heart, pancreas, testes, and epididymal fat were quickly harvested and weighed. Liver and kidney were placed into plastic screwtop containers and stored at −80° C. for further analysis.

Blood Chemistry

Blood was collected from the tail after four, eight, and twelve weeks of Cr or $H_2O$ administration. Prior to blood collection, animals were fasted 12 to 15 hours.

Immediately after blood removal, 0.5 mg/mL heparin and 10 mg/mL NaF were added to the blood. Blood was next immediately centrifuged; the blood plasma was tested for glucose, total cholesterol, triglycerides, low density lipoprotein (LDL) cholesterol (week 12 only), and high density lipoprotein (HDL) cholesterol (week 12 only) using Diagnostic Kits from Sigma Chemical Co. (St. Louis, Mo.) and insulin using double antibody or antibody coated kits from ICN Biomedicals (Costa Mesa, Calif.).

Metal Analyses

Determinations of chromium and iron concentrations were performed by Galbraith Laboratories (Knoxville, Tenn.).

Histology of Liver and Kidney Samples

The right kidney and a portion of the largest lobe of the liver were preserved in 10% buffered formalin phosphate. The organs from three randomly selected rats from each group were used for further analyses. Histopathological analyses were performed in the laboratory of Professor Thomas Bauman of the Department of Biological Sciences of The University of Alabama. Samples were stained with hematoxylin and eosin for analyses.

Statistical Analyses

Statistical analyses were performed by analysis of variance. All values are presented as mean±SEM. P values are calculated using standard deviations.

Results

Figure 1:
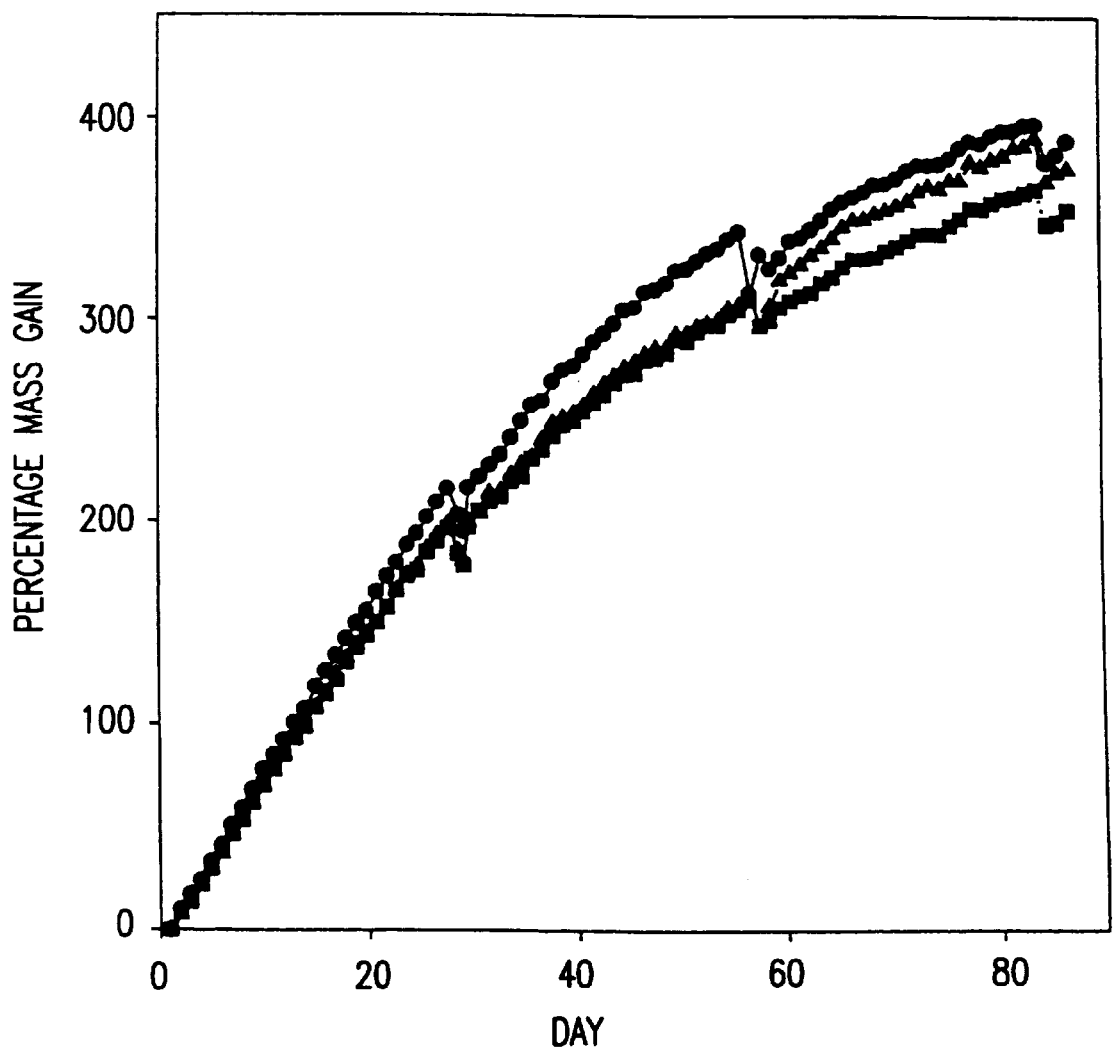
FIG. 1: Percentage body mass increase of control and rats supplemented with LMWCr and Compound 1. The spikes represent mass losses as a result of fasting before blood samples were taken. Circles—LMWCr, squares—1, and triangles—control.
Figure 2A:
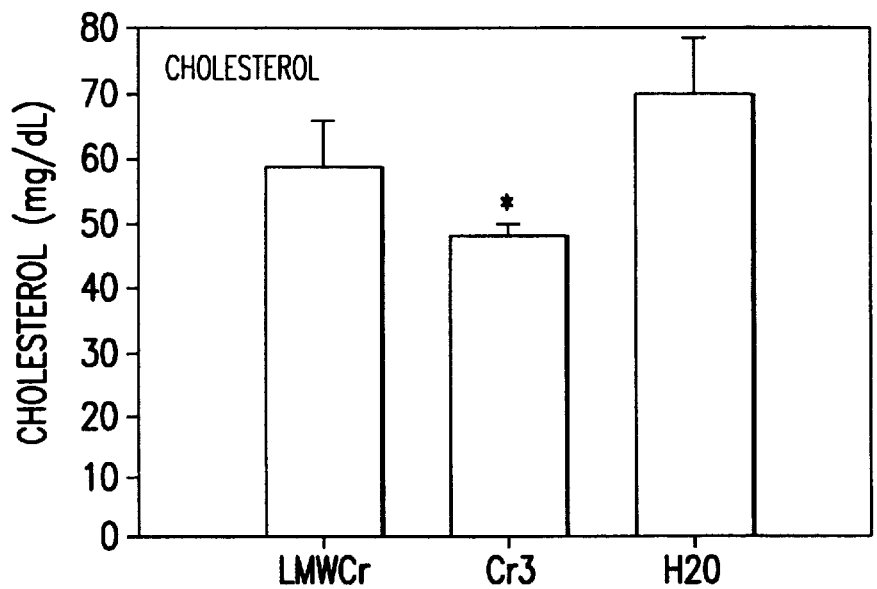
FIG. 2: Effect of Cr supplementation on plasma total cholesterol, HDL cholesterol, LDL cholesterol, and triglycerides and epididymal fat pad weight. *–P<0.05 for comparison between control and supplemented rats.
Figure 2B:
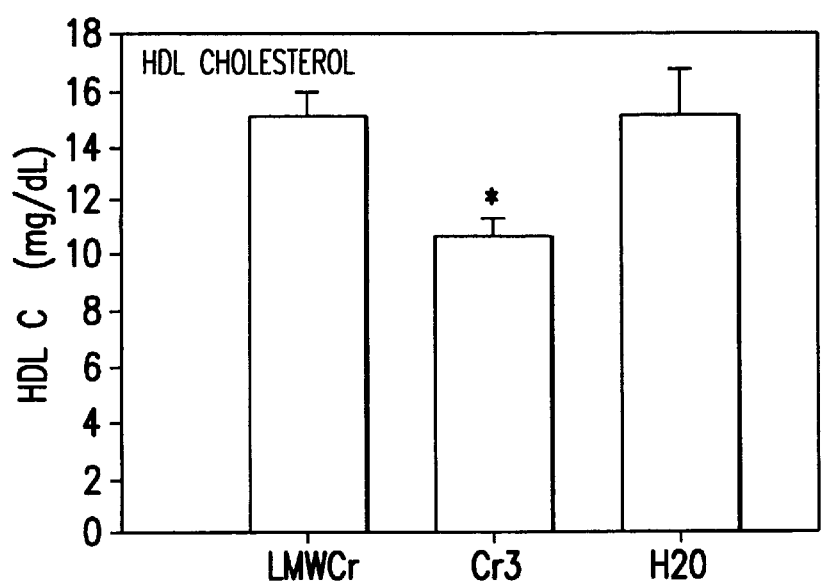
Figure 2C:
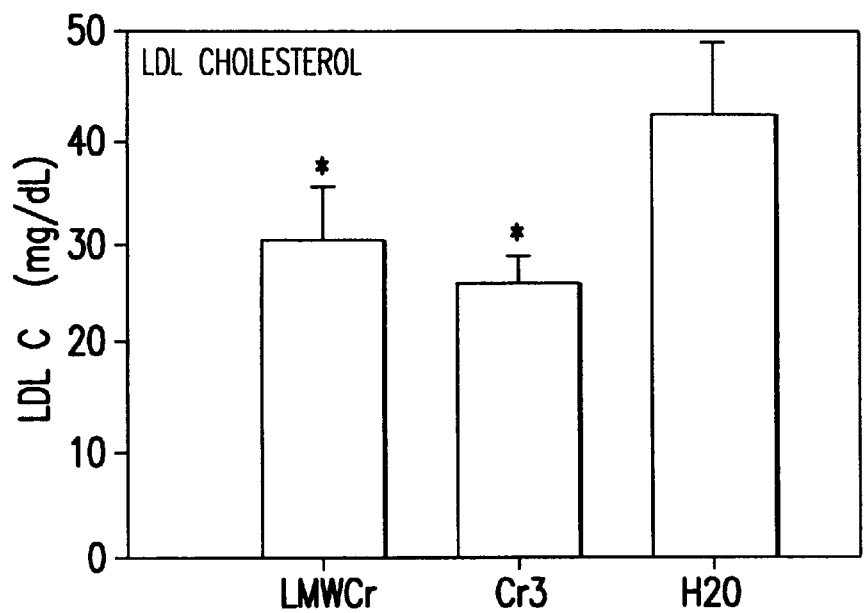
Figure 2D:
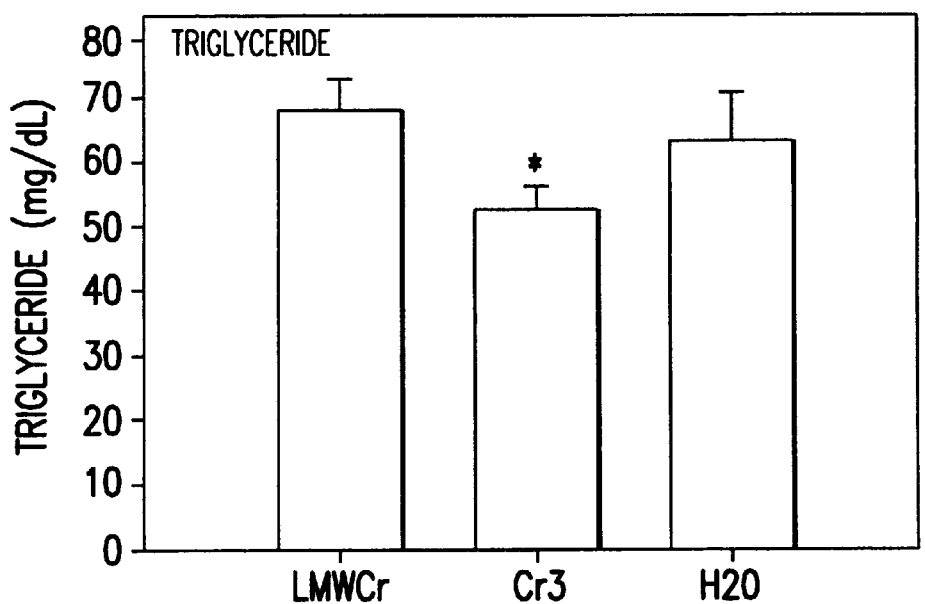
Figure 2E:
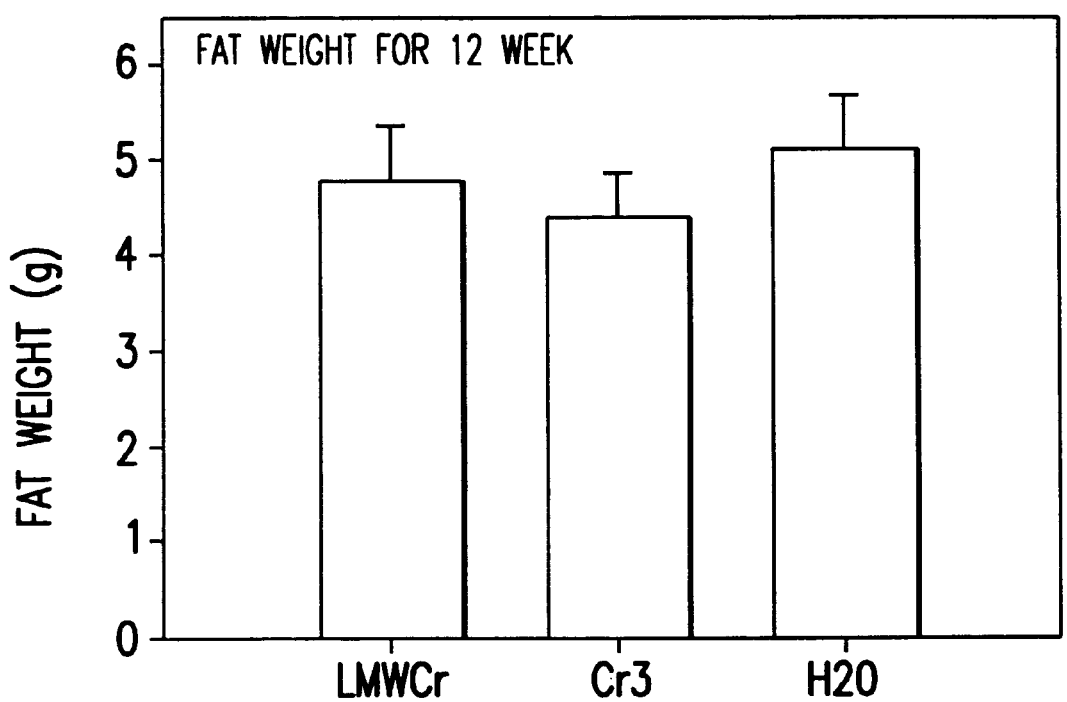

The daily food intake (not shown) and the daily percentage mass gain (average mass gain/average mass on day one×100%) of the control group and the chromium-supplemented groups (FIG. 1) were statistically equivalent throughout the 12 week period. All animals appeared normal throughout, and no visible differences were observed among the groups. Rats in the LMWCr-supplemented group had a slightly (but not statistically) higher percent mass gain over the first few weeks, but this was a reflection of the group starting with a slightly lower initial average mass (97.5±5.9 g verses 105.6±5.9 g for the control and 107.8±5.8 g for compound 1-supplemented rats) and disappeared as maturity was approached. Interestingly during the last few weeks of the study, the average mass of the compound 1-supplemented rats began to diverge from that of the other groups toward lower mass. This suggests the need for longer term studies to determine whether this trend would continue over time and become statistically significant. The lack of difference in body mass with chromium supplementation is consistent with numerous other studies [31–33, 53–55].

Organ masses after twelve weeks of supplementation did not differ statistically from those of the control for the heart, liver, kidney, and epididymal fat pads (Table 1). No organs were visibly different for any of the groups. For both the LMWCr-and compound 1-supplemented groups, the pancreas was enlarged, and the testes were smaller for the compound 1 group. The smaller testes are reminiscent of the effect of a chromium-enriched (i.e., chromium-deficient diet plus added chromium) versus a chromium-deficient diet [34] and interesting in relationship to a study that observed increased sperm count and fertility in male rats fed a Cr-enriched diet versus those on a Cr-deficient diet [56]. The increased pancreas size may also be of note as Anderson and coworkers have reported that Cr deficient diets have an effect on rat pancreas [57].

Blood variables were determined for all three groups after 4, 8, and 12 weeks of supplementation (Table 2). At each time, the plasma glucose concentrations were equivalent among the groups. The only significant differences observed after 4 or 8 weeks were the triglyceride concentration for the LMWCr-supplemented group at week 4 and the plasma insulin concentration for the compound 1-supplemented group at week 8. However, neither of these apparent differences is confirmed at week 12. Yet at week 12, a major trend is indicated as the triglyceride, total cholesterol, LDL cholesterol, and HDL cholesterol concentrations are all low for the compound 1-supplemented group. For example, the LDL cholesterol concentration in this group is nearly 40% less than that of the control, and total cholesterol concentration of the group is 33% less than that of the control. The LDL cholesterol level for the LMWCr-supplemented rats is also statistically lower than that of the control. The lack of effect on fasting glucose concentrations is consistent with results of recent studies using other forms of chromium as supplements [31–33], but the effects on cholesterol and triglyceride levels are in stark contrast to these studies. The lack of effect on glucose concentrations is also consistent with recent studies of the effect of a Cr deficient diet on rats versus a Cr-enriched diet and a normal diet [55,58]. Thus, no effect on fasting glucose levels is expected for supplementation. The lack of an effect of compound 1 supplementation on insulin levels at week 12 may be surprising given the effects on triglycerides and cholesterol. However, studies on Cr-deficient rats and rats on a Cr-enriched diet versus those on a normal diet by the same research laboratory [55,58] have shown some interesting results. Cr-enriched diets resulted in increased plasma insulin after 12 weeks, while the Cr deficient diet resulted in only a small increase versus the control; however, after 24 weeks, all animals had normal fasting insulin concentrations [55]. After 16 weeks in a second study, rats on the Cr-enriched diet had normal insulin levels while levels were raised in Cr-deficient rats [58]. Thus, it is unclear what should be expected for insulin levels, although the decreased fasting insulin levels for the compound 1-supplemented group at week 8 which became normal at week 12 becomes more interesting in light of these previous results. A tendency for Cr deficiency to raise triglyceride levels has been observed [58].

Histopathological analyses detected no differences in tissue samples from the kidneys or livers of any of the three groups.

Chromium has been suspected of potentially adversely affecting iron metabolism [8]. Thus, the iron and chromium levels of liver tissue from rats of each group were examined. In all cases, chromium concentrations in dried liver were less than 2 $\mu$g per g dry mass. Twelve weeks of compound 1 supplementation had no effect on iron concentration ($6.0 \times 10^2$ $\mu$g/g dry mass vs. $6.1 \times 10^2$ $\mu$g/g dry mass for control livers). Livers of rats supplemented with LMWCr had a decreased iron content ($3.8 \times 10^2$ $\mu$g/g dry weight).

Discussion

Chromium(III) is generally regarded a nutrient, not a therapeutic [59]. Consequently, an individual who is not deficient in chromium would not be expected to benefit from the intake of additional chromium. Most recent studies on the effects of Cr(pic)$_3$ or other chromium supplements on healthy individuals observed no beneficial effects from supplementation [8, 60–63], as one would expect which if such individuals are not chromium deficient. The only conclusive demonstration of chromium deficiency in humans is in patients receiving parenteral nutrition [64]. Current dietary guidelines for chromium intake are too high for both adults and infants, and no specific data are available on which to base recommendations for children and adolescents [65]. Similarly, observations of effects of diet supplementation with chromium on rats requires strict environmental control, such as the removal of any stainless steel objects, to guarantee chromium deficiency [1–5, 54]. Hence, supplementation of the diet of healthy rats on a normal diet with absorbable sources of chromium should have no effect as has been observed previously [31–34, 53].

The observation that chromium(III) serves as a nutrient and not a therapeutic is easily rationalized based on the proposed mechanism of chromium action [7]. The biologically active form of chromium, LMWCr, is maintained in insulin-sensitive cells in its apo (metal-free) form. In response to insulin, chromium concentrations in the blood decrease as chromium is moved to insulin-sensitive cells [66–68]. LMWCr has a large chromic ion binding constant and becomes loaded with the metal ion. The holoLMWCr is consequently primed so that, in the presence of insulin, insulin receptor tyrosine kinase is activated and held in its active form; consequently, chromium is proposed to act as part of an insulin signaling autoamplification mechanism [7]. If sufficient chromium is maintained in the blood (probably in the form of chromium transferrin [69]), supplemental chromium should have no beneficial effect. However, one possible mechanism is available by which chromium could potentially act with beneficial effect in healthy individuals. If the concentration of the biologically active form of chromium, holoLMWCr, or a functional mimetic could be increased in insulin-sensitive cells, this could trap insulin-stimulated insulin receptor in its active conformation, resulting in increased insulin signaling and subsequent cellular action. This experiment tests this hypothesis.

As demonstrated in FIG. 2, the functional biomimetic, compound 1, has a striking effect on plasma triglycerides, total cholesterol, LDL cholesterol, and HDL cholesterol levels after 12 weeks of supplementation. Interestingly, the average mass of epididymal fat follows the same pattern, being lowest (but not statistically lower than the control) in the compound 1-supplemented group. However, the fat content is statistically lower at the level of standard error used by some researchers (rather than the more rigorous standard deviation criterion utilized herein). The effects by compound 1 on cholesterol and triglycerides and potentially epididymal fat and body weight with continuing supplementation suggest that the trinuclear complex serves not as simply a chromium source but possesses an intrinsic activity, in stark contrast to other sources of chromium previously examined. Also no toxic effects were observed for supplementation with compound 1. These results suggest that compound 1 may have potential as a therapeutic; thus, the approach of identifying and characterizing the naturally-occurring, biologically active form of chromium and using this data to develop and design potential therapeutics seems to be rational. Contrastingly, LMWCr, as might have been expected from its susceptibility to hydrolysis, susceptibility to attack by proteases, and potential to be recognized and excreted, probably does not survive intact in the rat.

TABLE 1

Tissue masses of control and rats supplemented with LMWCr or Compound 1. Values are means ± SEM with eight rats per group. Masses are in grams.

| Tissue | Control | LMWCr | 1 |
|---|---|---|---|
| Heart | 1.51 + 0.06 | 1.56 + 0.08 | 1.43 + 0.19 |
| Liver | 19.80 + 1.07 | 18.91 + 0.84 | 19.55 + 0.64 |
| Kidney | 2.26 + 0.07 | 2.28 + 0.12 | 2.36 + 0.08 |
| Pancreas | 0.70 + 0.08 | 1.33 + 0.23* | 1.42 + 0.19* |
| Testes | 3.68 + 0.11 | 3.31 + 0.24 | 3.33 + 0.19* |
| Epididymal fat | 5.14 + 0.55 | 4.79 + 0.59 | 4.44 + 0.45 |

*–$P < 0.05$ for comparison between control and supplemented rats.

TABLE 2

Effects of LMWCr and Compound 1 on plasma variables after 4, 8, and 12 weeks of supplementation. Values are mean ± SEM weight eight rats per group.

| | Glucose (mg/dL) | Total cholesterol (mg/dL) | Triglycerides (mg/dL) | Insulin ($\mu$IU/mL) | LDL cholesterol (mg/dL) | HDL cholesterol (mg/dL) |
|---|---|---|---|---|---|---|
| Week 4 | | | | | | |
| Control | 116 ± 23 | 71.4 ± 5.6 | 81.1 ± 5.6 | 99.5 ± 3.9 | N.D. | N.D |
| LMWCr | 157 ± 14 | 78.9 ± 4.9 | 65.2 ± 4.3* | 100 ± 3.3 | N.D. | N.D. |
| 1 | 168 ± 33 | 65.2 ± 3.4 | 83.3 ± 2.7 | 99.0 ± 3.2 | N.D. | N.D. |
| Week 8 | | | | | | |
| Control | 79.4 ± 3.1 | 71.6 ± 7.3 | 48.5 ± 5.8 | 70.0 ± 4.3 | N.D. | N.D. |
| LMWCr | 76.6 ± 1.9 | 86.7 ± 5.7 | 42.3 ± 2.7 | 63.3 ± 3.5 | N.D. | N.D. |
| 1 | 75.5 ± 2.9 | 63.8 ± 3.3 | 41.8 ± 2-1 | 43.3 ± 2.1* | N.D. | N.D. |
| Week 12 | | | | | | |
| Control | 66.5 ± 3.2 | 69.8 ± 9.1 | 64.3 ± 7.8 | 42.0 ± 2.4 | 41.9 ± 6.8 | 15.1 ± 1.6 |
| LMWCr | 71.4 ± 2.0 | 58.7 ± 5.9 | 68.9 ± 4.7 | 40.0 ± 2.5 | 29.9 ± 5.2* | 15.1 ± 0.90 |
| 1 | 68.2 ± 2.8 | 46.9 ± 2.8* | 53.2 ± 3.7* | 43.0 ± 1.9 | 25.6 ± 2.4* | 10.7 ± 0.65* |

N.D. – not determined.
*$P < 0.05$ for comparison between control and supplemented rats.

Example 2

Analysis of DNA Cleavage by Low-Molecular-Weight Chromium-Binding Substance and Biomimetic $[Cr_3O(O_2CCH_2CH_3)_6(H_2O)_3]^+$ Under Physiologically-Relevant Conditions Summary The DNA-cleaving abilities of LMWCr and 1 in the presence of biological reductants such as ascorbate and thiols or in the presence of hydrogen peroxide were examined. This study demonstrated that LMWCr and the biomimetic 1 are much less able to effect this type of damage to DNA under physiologically-relevant conditions than Cr(pic)$_3$. This work demonstrates that these complexes, unlike Cr(pic)$_3$, are poor DNA-cleaving agents and may, therefore, be safer materials for human consumption.

Experimental

All manipulations were performed under aerobic conditions at room temperature, and all chemical were used as received unless otherwise noted. Bovine liver LMWCr was isolated and purified according to a known procedure. [Cr$_3$O(O$_2$CCH$_2$CH$_3$)$_6$(H$_2$O)$_3$]$^+$1, (CrO(OAc)$_6$(H$_2$O)$_3$]Cl, and Cr(pic)$_3$.H$_2$O were synthesized according to known procedures. pUC19 plasmid DNA was obtained from Bayou Biolabs and was gel-purified and quantitated by ultraviolet spectroscopy, using a Pharmacia Ultrospec 2000 spectrophotometer, prior to use in reactions. Superoxide dismutase (SOD) and catalase were obtained from Sigma.

DNA Cleavage Reactions

A typical reaction was carried out mixing aliquots of pUC19 (in 5 µM Tris, 500 EDTA buffer (pH 8.0)), reductant in H$_2$O, LMWCr in 50 mM NH$_4$OAc (pH 6.5) or 1 in H$_2$O, phosphate buffer (pH 7.0), and H$_2$O to give a final volume of 15 µL; the final phosphate concentration was 50 mM. Inhibitors were added as solutions in H$_2$O, solutions in phosphate buffer, or as neat liquids. Reactions were allowed to proceed 180 minutes unless otherwise noted. All reactions were quenched by addition of loading buffer (24% glycerol and 0.1% bromophenol blue). Seven microliter aliquots were loaded directly onto a 1% agarose gel and electrophoresed at 60 V. The gel was stained with ethidium bromide and was photographed on a UV transilluminator. Any timed assays were performed by adding the appropriate reagents to the sample tubes, and the addition of DNA was marked time zero. The reactions were quenched at various time points by adding loading buffer. Reactions under argon were performed by bubbling the gas through the reaction mixture until all the reagents were added and then sealing the container until the reaction was quenched by addition of loading buffer.

Effect of Nicked DNA on Cell Viability

A reaction mixture containing 10 µg of pUC19, 1.5 mM 1, and 0.900 mM H$_2$O in 10 mM Tris, pH 8.0 was allowed to react for 3 hours at 25° C. Quench buffer was added, and the sample was immediately loaded onto a 1% agarose gel containing 0.5 µg ml$^{-1}$ of ethidium bromide. After electrophoresis in 1×TBE buffer, the band at 3.5 kB was excised from the gel, and the DNA was removed from the gel using a Qiagen gel purification kit. The eluted DNA was gel-quantitated and used without further modification for transformation.

Electrocompetent DH5α E. coli cells were electroporated using 1 µL of 0.1 µg mL$^{-1}$ of either trimer-nicked DNA or supercoiled pUC19 plasmid DNA in 50 µL of cells. The E. coli cells were rescued by adding 1 mL of SOC media (20 gL$^{-1}$ Bactotryptone, 5 gL$^{-1}$ yeast extract, 9 mM NaCl, 20 mM glucose, pH 7.5), followed by incubation at 37° C. for 1 hour. Each cell suspension was diluted 1:100 with SOC media, and 50 µL of each diluted suspension was spread on separate LB-ANM agar plates containing 80 µg mL$^{-1}$ X-gal, 100 µM IPTG, and 100 µg mL$^{-1}$ ampicillin. The X-gal and IPTG were added to facilitate detection of colonies. The plates were placed in a 37° C. incubator overnight. The transformation efficiency of relaxed plasmid DNA is comparable to that of supercoiled pUC19 plasmid DNA under these conditions.

Phosphate Mono- and Diester Hydrolysis Reactions

Phosphate mono- and diester hydrolysis reactions were monitored on an HP8452 diode-array LTV-Vis Spectrophotometer at 25° C., measuring the production of p-nitrophenol at 404 nm. Multiple trials were performed for each set of reactions. Background reactions of phosphate mono- and diester compound alone, with H$_2$O$_2$, and with 1 were used to correct any observed activities. Typical reaction mixtures contained 1.25 mM bis-p-nitrophenyl phosphate or 2.5 mM p-nitrophenyl phosphate, 1.5 mM 1, and 900 µM H$_2$O$_2$ in freshly prepared, chelexed 0.010 M Tris, pH 8.0. Rates were calculated using $\epsilon_{404}$ for p-nitrophenol at pH 8.0 of 17,000$^{-1}$ M cm$^{-1}$.

DNA Cleavage by Complex 1

Figure 3:
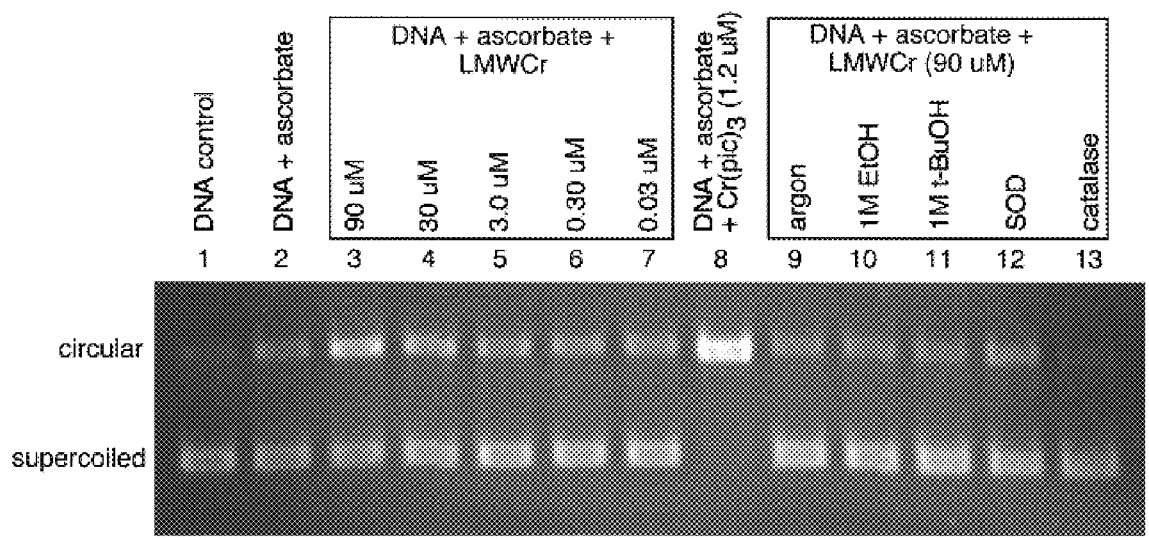
FIG. 3: Cleavage of pUC19 by compound 1. The reactions contain pUC19 (39 $\mu$M in base pairs) and 50 $\mu$M phosphate buffer, pH 7.0, and: Lane 2, 5 MM ascorbate; Lanes 3–7, 5 mM ascorbate and 120, 40, 4.0, 0.40, and 0.040 $\mu$M 1, respectively; Lane 8, 5 mM ascorbate and 1.2 $\mu$M Cr(pic)$_3$; Lane 9, 5 mM ascorbate and 120 pM 1 under argon; Lane 10, 5 mM ascorbate, 120 $\mu$M 1, and 1 M EtOH; Lane 11, 5 mM ascorbate, 120 $\mu$M 1, and 1 M t-BuOH; Lane 12, 5 mM ascorbate, 120 $\mu$M 1, and 100 $\mu$g/mL SOD; and Lane 13, 5 mM ascorbate, 120 $\mu$l , and 100 $\mu$/mL catalase. Reactions were allowed to proceed 60 minutes before quenching.
Figure 4:
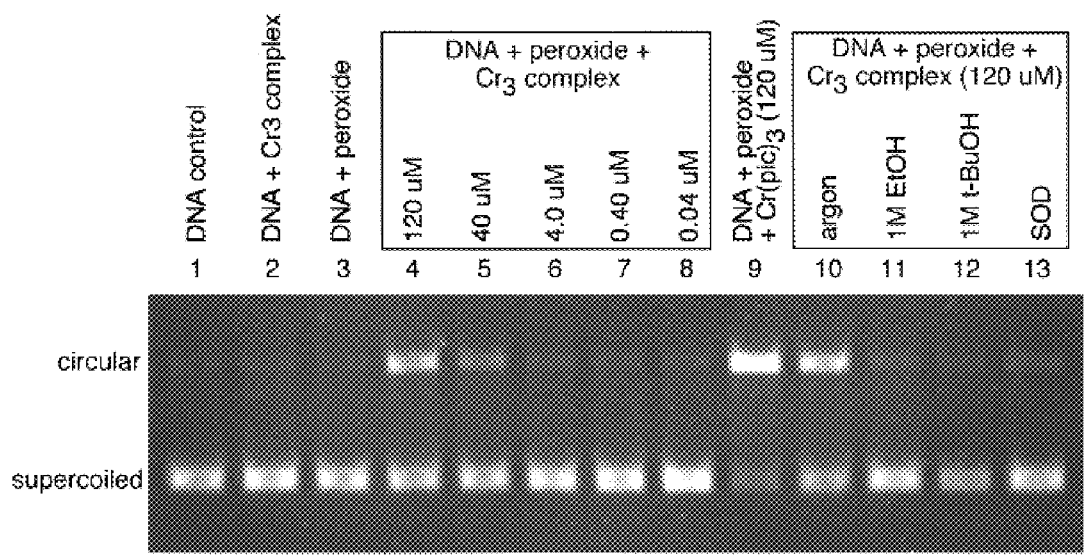
FIG. 4: Cleavage of pUC19 by compound 1. The reactions contain pUC19 (39 $\mu$M in base pairs) and 50 mM phosphate buffer, pH 7.0, and: Lane 2, 120 $\mu$M 1; Lane 3, 215 $\mu$M H$_2$O$_2$; Lanes 4–8, 215 $\mu$M H$_2$O$_2$ and 120, 40, 4, 0.4, and 0.04 pM 1, respectively; Lane 9, 215 $\mu$M H$_2$O$_2$ and 120 $\mu$M Cr(pic)$_3$; Lane 10, 215 $\mu$M H$_2$O$_2$ and 120 $\mu$M 1 under argon; Lane 11, 215 $\mu$M H$_2$O$_2$, 120 $\mu$M 1, and 1 M EtOH; Lane 12, 215 $\mu$M H$_2$O$_2$, 120 $\mu$M 1, and 1 M t-BuOH; and Lane 13, 215 $\mu$M H$_2$O$_2$, 120 $\mu$M 1, and 100 $\mu$g/mL SOD.

The reaction of trinuclear Cr(III) propionate complex, 1, with pUC19 was monitored by observing the conversion of the supercoiled plasmid DNA (faster migrating species) to the circular, nicked form (slower migrating species). All reactions were evaluated by comparison of the amount of relaxed plasmid to the amount in gel-purified plasmid controls. In the presence of the biological reductant ascorbic acid (and atmospheric oxygen), plasmid DNA is slowly nicked (FIG. 3, Lane 2); this is a long known phenomenon and appears to result in part from the production of hydroxyl radicals. The addition of 1 to the mixture of ascorbate and DNA, regardless of concentration (in the range examined, 0.040 to 120 µM), has no effect the amount of relaxed DNA (FIG. 3, Lanes 3–7). Given that 1 by itself has no effect on the rate of DNA cleavage (FIG. 4, Lane 2), the trimer appears to be ineffective in catalyzing the cleavage of DNA in the presence of ascorbate and oxygen. Similar results are obtained for 1 in the presence of the reductant dithiothreitol: DTT under aerobic conditions produces some cleavage of the plasmid DNA while addition of 1 does not increase the amount of cleavage (not shown). The cleavage in the presence of ascorbate (and of 1) is time dependent (not shown) and is inhibited in the absence of oxygen (FIG. 3, Lane 9) the presence of the radical traps EtOH and t-BuOH (FIG. 3, Lanes 10 and 11), and the presence of superoxide dismutase or catalase. These results are consistent with the mechanism of DNA cleaving involving the reduction of dioxygen by ascorbate to give radical products capable of cleaving DNA.

These results are in stark contrast to those using Cr(pic)$_3$ as a chromium source. As shown in FIG. 3 (Lane 8), Cr(pic)$_3$ (at a chromium concentration of 1.2 µM, equivalent to that of the trimer in Lane 6) is quite effective in generating relaxed DNA from supercoiled plasmid DNA in the presence of 5 µM ascorbate. Significantly, these concentrations of Cr(pic)$_3$ and ascorbate are physiologically relevant. It has been predicted that a person consuming 5.01 mg of Cr(pic)$_3$, equivalent to three pills of some common supplements, daily for five years would have a liver Cr concentration of 13 pm, more than ten times the Cr(pic)$_3$ concentration used in this experiment. Ascorbate concentrations in most tissues, including liver, are in the millimolar range. The ability of Cr(pic)$_3$ to catalyze cleavage of DNA under these conditions stems from the presence of the picolinate ligands. The aromatic, bidentate ligands coordinated via pyridine-type nitrogens modify the redox potential of the central chromic ion such that it can be reduced by ascorbate or thiols; dioxygen oxidizes the chromium center back to Cr(III) with concurrent reduction of dioxygen. This reduced dioxygen-derived species can undergo O—O bond cleavage, generating OH which may diffuse to react with DNA. The resulting Cr species may again be reduced and reenter the catalytic cycle. Consequently, it is not surprising that $Cr(pic)_3$ has been found to lead to DNA strand breaks in cultured Chinese hamster ovary cells [36] and cultured macrophages. (However, it should be noted that a recent study failed to find oxidative DNA damage using an antibody titer to 5-hydroxymethyl uracil for ten obese women taking $Cr(pic)_3$ for eight weeks.) The trinuclear 1 lacks any type of nitrogen-based ligation and, thus, is not susceptible to reduction by ascorbate or thiols. Correspondingly, chromium acetate hydroxide ($\{[Cr_3O(OAc)_6]OAc\}_x$, a polymeric array of oxo-centered trinuclear assemblies which breaks apart to give the acetate analogue of 1) at sub-cytotoxic concentrations has been found to fail to produce DNA strand breaks in peripheral lymphocytes. The acetate analogue of 1, $[Cr_3O(OAc)_6(H_2O)_3^+]$, has previously been shown to be unable to catalyze DNA cleavage in the presence of ascorbate, consistent with the results of this study on complex 1.

Previously these laboratories have shown that the trinuclear complex $[Cr_3O(OAc)_6(H_2O)_3]^+$ was capable of relaxing plasmid DNA in a time- and concentration-dependent fashion in the presence of large concentrations of hydrogen peroxide; this cleavage appeared to result from the formation of hydroxyl radical from peroxide catalyzed by the trinuclear species. Given the strong similarities between this compound and its propionate analogue, 1, the ability of complex 1 to cleave DNA in the presence of peroxide was probed. As shown in Lanes 4–8 of FIG. 4, the trimer catalyzes the cleavage of DNA in the presence of peroxide in a concentration dependent fashion, although the reaction is extremely slow. The reaction catalyzed by the acetate analogue of 1 and peroxide in pH 7.0 phosphate buffer results in a degree of cleavage indistinguishable from produced by complex 1 (not shown). The small degree of cleavage obtained in these experiments required a three hour reaction time. The cleavage of DNA is also time dependent (not shown). The rate of cleavage is not affected by removing atmospheric oxygen but is inhibited by the radical traps ETOH and t-BuOH. The mechanism for this cleavage probably corresponds to that proposed previously for the acetate analogue. Hydrogen peroxide presumably displaces a carboxylate ligand and bridges between two chromic centers. Homolytic cleavage of the hydrogen peroxide, catalyzed by the trimers, produces two equivalents of hydroxyl radical. The OH species diffuse to react with DNA. SOD also has an inhibitory effect on the reaction, suggesting that superoxide produced from peroxide may also play a role in the cleavage reactions. Previously, reactions with the acetate analogue in Tris buffer (rather than phosphate buffer) have failed to detect any inhibition from SOD; the Tris may serve as a suitable trap for superoxide radicals, such that this side pathway to radical-based cleavage was not observed.

$Cr(pic)_3$ has been shown to generate hydroxyl radicals from hydrogen peroxide in a pathway independent of added reductant. This pathway is, however, orders of magnitude less efficient than that in the presence of reductant, although the rate of cleavage catalyzed by the nutritional supplement still far exceeds that of trinuclear complex 1 under identical conditions. This is readily demonstrated in FIG. 4 (Lane 9); in the presence of 215 $\mu$M peroxide, 120 $\mu$M $Cr(pic)_3$ gives rise to a much greater quantity of relaxed DNA than does 1 at equivalent or higher Cr concentrations (Lanes 5 and 4, respectively). Generation of hydroxyl radicals from hydrogen peroxide in a pathway independent of added reductant has also been observed for other mononuclear Cr(III) complexes; however, the efficiency of such pathways are roughly equivalent to that of $Cr(pic)_3$ and probably not responsible for the mutagenic effects of Cr(III), which require added reductants.

The different chemistry observed with the trinuclear complex and with $Cr(pic)_3$ is readily borne out by their redox potentials. Oxo-centered trinuclear chromic carboxylates are electrochemically inactive in water, such that they are far too difficult to reduce for ascorbate or thiols to serve as reducing agents. In contrast, previous spectroscopic and electrochemical studies place the redox potential for the metal-centered reduction of $Cr(pic)_3$ in the range of those for chromium(III) complexes known to give rise to oxygen radical-mediated DNA damage, as well as in the range of the redox potential of biological reductants such as ascorbate, thiols, and NADH.

DNA Cleavage by LMWCr

Spectroscopic studies on LMWCr suggest that its chromic centers possess primarily, if not solely, oxygen-based ligands; consequently, LMWCr is not expected to catalyze DNA cleavage in the presence of mild reductants. This is also born out by the technique used to remove chromium from the oligopeptide to produce the apo-oligopeptide. Chromium is removed by chelation with EDTA at acidic pH's at circa 60° C.; however, for the chromium to be removed, it must be reduced to the chromous state. Ascorbate and thiols are ineffective; cyanoborohydride is required for the reduction.

As shown in FIG. 5 (Lanes 3–7), LMWCr in the presence of 5 mM ascorbate actually does catalyze the cleavage of DNA in a concentration dependent fashion to a detectable extent; however, the degree of cleavage is all but insignificant in comparison with that of $Cr(pic)_3$ at an equivalent chromium concentration of 1.2 $\mu$M (FIG. 5, Lanes 6 and 8). An effort was made to examine the inhibition of the LMWCr-catalyzed cleavage by a variety of inhibitors but the amount of catalyzed cleavage is of the same order of magnitude of cleavage by ascorbate itself; consequently, the effects of the inhibitors on the cleavage reaction initialed by ascorbate and oxygen could not be separated from effects on the inhibition of the LMWCr-catalyzed process. Cleavage of DNA by hydrogen peroxide is also catalyzed by LMWCr but to an extent even less than that of complex 1 (FIG. 6, Lanes 4–8). An appreciable amount of cleavage can be observed only at the highest LMWCr concentration examined (90 $\mu$M, 360 $\mu$M Cr). This is in stark contrast to $Cr(pic)_3$ (FIG. 6, Lane 9) where at a three-fold lower concentration (in terms of chromium) nearly all the plasmid DNA is nicked. Oxygen is not required for the cleavage in the presence of peroxide, while the cleavage is apparently inhibited to some degree by ETOH, t-BuOH, and SOD (FIG. 6, Lanes 10–13), although the low levels make this difficult to determine.

Effect of DNA Nicking on Cell Viability

For the cleavage of DNA to have serious deleterious effects on the cells containing the damage, the damage must not be readily repairable. The transformation of *E. coli* cells with plasmid DNA, before and after incubation with complex 1, provides a convenient and accurate measure of whether complex-mediated DNA damage (although generated at peroxide concentrations far above physiological levels) was irreversible. As the plasmid carries an antibiotic resistance gene marker for ampicillin, only *E. coli* cells that possess intact plasmid DNA will be able to grow on media plates containing AMP. Complex-nicked DNA was generated by incubating the DNA for 3 hrs with complex and peroxide. The nicked band was excised from the gel, gel-quantitated, and used to transform E. coli cells; additionally an equal concentration of supercoiled pUC19 was used to transform cells. The transformed cells were then plated on LB plates containing ampicillin. As shown in FIG. 5, the plate with cells transformed with nicked DNA contained the same number of colonies (within the relative error of the gel-quantitation method) as the positive control. (It has previously been shown that transformation of cells with nicked DNA (produced by prolonged storage of pUC19) results in an appreciable reduction of colonies present [46]). Thus, the E. coli DNA repair enzymes could repair the damage produced by incubation with the trimer and peroxide. Consequently, the likelihood that the use of complex 1 as a nutritional agent would lead to irreversible DNA cell damage would appear remote.

Phosphate Ester Cleavage Reactions

Previously $[Cr_3O(OAc)_6(H_2O)_3]^+$ has been shown to hydrolyze both phosphate mono- and diesters in the presence of hydrogen peroxide while the complex or peroxide by itself were ineffective [46]. The cleavage was proposed to be performed by Cr(IV)-hydroxide species (in equilibrium with Cr(III)-hydroxyl radical species) produced by the homolytic cleavage of peroxide catalyzed by the trinuclear complex. Consequently, the ability of complex 1 to hydrolyze the phosphate monoesterp-nitrophenyl phosphate and phosphate diester bis-p-nitrophenylphosphate was investigated. Complex 1 does hydrolyze both phosphate ester compounds with similar rate constants in the presence of peroxide (FIG. 8). The rate is approximately one-fourth order in phosphate ester, is one-half order in peroxide, and has a complex dependence on the trimer concentration.

LMWCr has previously been shown not to possess phosphatase activity. As the oligopeptide is susceptible to hydrolysis, no attempt was made to probe the ability of LMWCr to catalyze the hydrolysis of phosphate esters in the presence of peroxide.

Abbreviations pic, picolinate; LMWCr, low-molecular-weight chromium-binding substance; SOD, superoxide dismutase; DTT, dithiothreitol; AMP, ampicillin; DNA, deoxyribonucleic acid; EDTA, ethylenediamine tetraacetic acid; E. coli, Escherichia coli; kB, kilobase; LB, Luria-Bertani; TBE, 45 mM Tris-45 mM borate-1 mM EDTA; Tris, tris (hydroxymethyl)aminomethane; X-gal, 5-bromo-4-chloro-3-indolyl-β-D-galactopyranoside.

Obviously, numerous modifications and variations of the present invention are possible in light of the above teachings. It is therefore to be understood that within the scope of the appended claims, the invention may be practiced otherwise than as specifically described herein.

References

1. Schwarz K, Mertz W (1959) Arch Biochem Biophys 85: 292–295.
2. Mertz W, Schwarz K (1959) J Physiol 196: 614–618.
3. Mertz W, Roginski E E, Schwarz K (1961) J Biol Chem 236: 318–322.
4. Mertz W, Roginski E E (1963) J Biol Chem 238: 868–872.
5. Mertz W, Roginski E E, Schroeder H A (1965) J Nutr 86: 107–112.
6. Davis C M, Vincent J B (1997) J Biol Inorg Chem 2: 675–679.
7. Vincent T B (1999) J Am Coll Nutr 18: 6–12.
8. Lukaski H C (1999) Ann. Rev. Nutr. 19: 279–301.
9. Anderson R A, Koziovsky A S (1985) Am J Clin Nutr 41: 768–771.
10. Anderson R A (1994) In: Mertz W, Abernathy C O, Olin S S (eds) Risk Assessment of Essential Elements. ISLI Press, Washington, pp 187–196.
11. Anderson R A (1998) J Am Coll Nutr 17: 548–555.
12. Schwarz K, Mertz W (1957) Arch Biochem Biophys 72: 515–518.
13. Toepfer E W, Mertz W, Polansky M M, Roginski W W, Wolf W R (1977) J Agric Food Chem 25: 162–166.
14. Anderson R A, Brantner J H, Polansky M M (1998) J Agric Food Chem 26: 1219–1221.
15. Vincent J B (1994) J Nutr 124: 117–118.
16. Sumrall K K Vincent J B (1997) Polyhedron 16: 4171–4177.
17. Gonzalez-Vergara E, Hegenauer J, Saltman P (1982) Fed Proc 41: 286.
18. Haylock S J, Buckley P D, Blackwell L F (1983) J Inorg Biochem 18: 195–211.
19. Mirsky N, Weiss A, Dori Z (1980) J Inorg Biochem 13: 11–21.
20. Kumpulainen J, Koivistoinen P, Lahtinen S (1978) Bioinorg Chem 8: 419–429.
21. Votava H J, Hahn C J, Evans G W (1973) Biochem Biophys Res Commun 55: 312–319.
22. Gonzalez-Vergara E, Hegenauer J, Saltman P, Sabat M, Ibers J A (1982) Inorg Chim Acta 66: 115–118.
23. Gerdom L E, Goff E M (1982) Inorg Chem 21: 3847–3848.
24. Chang J C, Gerdom L E, Baenziger N C, Goff H M (1983) Inorg Chem 22: 1739–1744.
25. Cooper J A, Anderson B F, Buckley P D, Blackwell L F (1984) Inorg Chim Acta 91: 1–9.
26. Bradshaw J E, Grossie D A, Mullica D F, Pennington D E (1988) Inorg Chim Acta 141: 41–47.
27. Steams D M, Armstrong W H (1992) Inorg Chem 31: 5178–5184.
28. Evans G W, Pouchnik D J (1993) J Inorg Biochem 49: 177–187.
29. Evans G W, Bowman T D (1992) J Inorg Biochem 46: 243–250.
30. Evans G W, Meyer L (1992) Age 15: 134.
31. Hasten D L, Hegsted N L Keenan M J, Morris G S (1997) Nutr Res 17: 283–294.
32. Hasten D L, Hegsted M. Keenan M J, Morris G S (1997) Nutr Res 17: 1175–1186.
33. Anderson R A, Bryden N A, Polansky M M (1997) J am Coll Nutr 6:273–279.
34. Anderson R A, Bryden N A, Polansky M M, Gautschi K (1996) J Trace Elem Exp Med 9:11–25.
35. Speetjens J K, Collins R A, Vincent J B, Woski S A (1999) Chem Res Toxicol, 12:483–487.
36. Stearns D M, Belbruno J J, Wetterhahn K E (1995) FASEB J 9: 1650–1657.
37. Sugden K D, Geer R D, Rogers S J (1992) Biochemistry 31: 11626–11631.
38. Davis C M, Vincent J B (1997) Biochemistry 36: 4382–4385.
39. Davis C M, Vincent J B (1997) Inorg Chem 36: 5316–5320.
40. Yamamoto A, Wada O, Suzuki H (1988) J Nutr 118: 39–45.
41. Davis C M, Vincent J B (1997) Arch Biochem Biophys 339: 335–343.
42. Harton A, Terrell K, Huffman J C, MacDonald C, Beatty A, Li S, O'Connor C, Vincent J B (1997) Inorg Chem 36: 4875–4882.
43. Donald S, Terrell K, Robinson K, Vincent J B (1995) Polyhedron 14: 971–976.

44. Ellis T, Glass M, Harton A, Folting K, Huffman J C, Vincent J B (1995) Inorg Chem 33:5522–5527.
45. Nagi M, Harton A, Donald S, Lee Y-S, Sabat M, O'Connor C J, Vincent J B (1995) Inorg Chem 34: 3813–3820.
46. Speetjens J K, Parand A, Crowder Vincent J B, Woski S A, Polyhedron, in press.
47. Johnson M K, Powell D B, Cannon R D (1981) Spectrochim Acta 37A: 995–1006.
48. Anderson R A, Polansky M M, Bryden N A, Roginski E E, Patterson K Y, Reamer D C (1982) Diabetes 31: 212–216.
49. Wada O, Wu G Y, Yamamoto A, Manabe S, Ono T (1983) Environ Res 32: 228–239.
50. Undenfriend S, Stein S, Bohlen P, Dairman W, Leimgruber W, Weigle M (1966) Science 178: 871–872.
51. Marczenko Z (1986)Spectrophotometric Determination of the Elements. Ellis Horwood, Chichester, England.
52. Earnshaw A, Figgis B N. Lewis J (1966) J Chem Soc A 1656–1663.
53. Morris G S, Guidry K A, Hegsted M, Hasten D L (1995) Nutr Res 15: 1045–1052.
54. O'Flaherty E J, McCarty C P (1978) J Nutr 108: 321–328.
55. Striffler J S, Law J S, Polansky M M, Bhathena S J, Anderson R A (1995) Metabolism 44:1314–1320.
56. Anderson R A, Polansky M M, (1981) Biol Trace Elem Res 3: 1–5.
57. Striffler J S, Polansky M M, Anderson R A (1993) J Trace Elem Exp Res 6: 75–81.
58. Striffler J S, Polansky M M, Anderson R A (1998) Metabolism 47: 396–400.
59. Anderson R A (1989) Sci Total Envir 86: 75–81.
60. Campbell W W, Joseph L J O, Davey S L, Cyr-Campbell D, Anderson R A, Evans W J (1999) J Appl Physiol 86: 29–39.
61. Walker L S, Bemben M G, Bemben D A, Knehans A W (1998) Med Sci Sports Exerc 30:1730–1737.
62. Lukaski H C, Bolonchuk W, Siders W A, Milne D B (1996) Am J Clin Nutr 63: 954–965.
63. Anderson R A (1998) Nutr Rev 56: 266–270.
64. Anderson R A (1995) Nutrition 11: 83–86.
65. Hunt C D, Stoecker B J (1996) J Nutr 126: S2441–S2451.
66. Morris B W, Gray T A, MacNeil S (1993) Clin Chem 84: 477–482.
67. Morris B W, MacNeil S, Stanley K, Gray T A, Fraser R (1993) J Endocrin 139: 339–345.
68. Morris B W, Blumsohn A, MacNeil S, Gray T A (1992) Am J Clin Nutr 55: 989–991.
69. Yamamoto A, Wada O, Ono T (1987) J Nutr 165: 627–631.

The references cited above are incorporated herein by reference.

The following are incorporated herein by reference in their entirety:

U.S. Pat. No. 5,872,102

U.S. application Ser. No.: 09/163,005, filed on Sep. 30, 1998 under Attorney Docket No. 772-073-27

Davis et al, Synthetic Multinuclear Chromium Assembly Activates Insulin Receptor Kinase Activity: Functional Model for Low-Molecular-Weight Chromium-Binding Substance, *Inorganic Chemistry*, Volume 36, Number 23, pp. 5316–5320

Speetjens al, The Nutritional Supplement Chromium(III) Tris(picolinate) Cleaves DNA, *Chemical Research in Toxicology*, Volume 12, No. 6, pp. 483–487.

What is claimed is:

1. A method of decreasing plasma cholesterol and/or triglycerides, comprising administering an effective amount of $[Cr_3O(O_2CCH_2CH_3)_6(H_2O)_3]^+$ to a patient in need thereof.

2. The method of claim 1, wherein the patient is a mammal.

3. The method of claim 1, wherein the patient is a human being.

4. The method of claim 1, wherein the patient is a dog, cat, cow, horse, chicken, turkey, sheep or a goat.

5. The method of claim 1, wherein cholesterol is decreased.

6. The method of claim 1, wherein triglycerides are decreased.

7. The method of claim 1, wherein the $[Cr_3O(O_2CCH_2CH_3)_6(H_2O)_3]^+$ is administered to the patient at a dose of 1 to 100 µg/kg body mass.

8. The method of claim 1, wherein the $[Cr_3O(O_2CCH_2CH_3)_6(H_2O)_3]^+$ is administered to the patient at a dose of 10 to 80 µg/kg body mass.

9. The method of claim 1, wherein the $[Cr_3O(O_2CCH_2CH_3)_6(H_2O)_3]^+$ is administered to the patient at a dose of 10 to 50 µg/kg body mass.

10. The method of claim 1, wherein the $[Cr_3O(O_2CCH_2CH_3)_6(H_2O)_3]^+$ is administered to the patient at a dose of 10 to 40 µg/kg body mass.

11. The method of claim 1, wherein the $[Cr_3O(O_2CCH_2CH_3)_6(H_2O)_3]^+$ does not cause DNA cleavage.

12. The method of claim 1, wherein the $[Cr_3O(O_2CCH_2CH_3)_6(H_2O)_3]^+$ is administered in the form of a food product.

13. The method of claim 1, wherein the $[Cr_3O(O_2CCH_2CH_3)_6(H_2O)_3]^+$ is administered in combination with at least one additional agent which is capable of reducing levels of plasma cholesterol and/or triglycerides.

14. A composition, comprising:

$[Cr_3O(O_2CCH_2CH_3)_6(H_2O)_3]^+$, and at least one additional agent which is capable of reducing levels of plasma cholesterol and/or triglycerides.

15. The composition of claim 14, wherein the additional agent is an inhibitor of cholesterol biosynthesis.

16. The composition of claim 14, wherein the additional agent is an inhibitor of β-hydroxy-β-methyl gluterate-coenzyme A (HMG-CoA) reductase or acyl CoA-acyl transferase (ACAT).

17. The composition of claim 14, wherein the additional agent is mevinolin or probucol.

* * * * *

UNITED STATES PATENT AND TRADEMARK OFFICE
CERTIFICATE OF CORRECTION

PATENT NO. : 6,149,948
DATED : November 21, 2000
INVENTOR(S) : John B. VINCENT

It is certified that error appears in the above-identified patent and that said Letters Patent is hereby corrected as shown below:

Column 6, line 59, "200 pL" should read --200 μL--.

Signed and Sealed this

Fifth Day of June, 2001

Attest:

*Attesting Officer*

NICHOLAS P. GODICI

*Acting Director of the United States Patent and Trademark Office*